United States Patent [19]

Drake et al.

[11] 4,271,057
[45] Jun. 2, 1981

[54] WATER SETTING ION-POLYMER CEMENTS

[75] Inventors: Cyril F. Drake, Harlow; Neil R. Adams, Wincle, near Macclesfield, both of England

[73] Assignee: International Standard Electric Corporation, New York, N.Y.

[21] Appl. No.: 91,915

[22] Filed: Nov. 6, 1979

[30] Foreign Application Priority Data

Nov. 8, 1978 [GB] United Kingdom ............... 43601/78

[51] Int. Cl.$^3$ ................................................ C08K 3/40
[52] U.S. Cl. ............................... 260/29.6 M; 106/35; 106/47 R; 106/52; 106/54; 260/998.11; 433/228
[58] Field of Search ................... 106/47 R, 54, 35, 52; 260/29.6 M, 998.11; 433/228

[56] References Cited

U.S. PATENT DOCUMENTS

| | | | |
|---|---|---|---|
| 3,814,717 | 6/1974 | Wilson et al. | 433/228 |
| 3,962,267 | 6/1976 | Suzuki et al. | 433/228 X |
| 4,123,416 | 10/1978 | Potter et al. | 106/52 X |
| 4,143,018 | 3/1979 | Crisp et al. | 433/228 |
| 4,166,744 | 9/1979 | Smith | 106/35 |
| 4,174,334 | 11/1979 | Bertenshaw et al. | 106/35 X |

OTHER PUBLICATIONS

Hirayama, C., J. Am. Cer. Soc. 44, pp. 602–606 (1961).

*Primary Examiner*—Helen M. McCarthy
*Attorney, Agent, or Firm*—John T. O'Halloran; Thomas N. Twomey

[57] ABSTRACT

In a water soluble glass composition for effecting cross-linking of a polycarboxylic acid cement, typically polyacrylic acid, the glass is treated with phosphorus pentoxide or a phosphate containing material. This inhibits the initial setting stage of the cement and thus prolongs the period within which the cement can be worked. The glass may be of the zinc oxide/boric oxide/alumina type or of the fluoroaluminoborosilicate type.

7 Claims, No Drawings

WATER SETTING ION-POLYMER CEMENTS

This invention relates to glass compositions such as are employed in the preparation of polycarboxylic acid water setting cements and to cement composition incorporating such glasses.

BACKGROUND OF THE INVENTION

It is well known that poly-carboxylic acid materials, such as polyacrylic acid can be cross-linked to form a solid cement by treatment with divalent or polyvalent metal ions. Typically the metal ion comprises zinc and or calcium. Recent work has shown that the metal ions required for cross-linking such cements may be supplied by glass compositions which may or may not completely dissolve in water as the cement sets.

When preparing water setting cement compositions in which a glass material provides the cross-linking means two stages of setting of the material are observed. During the first stage the viscosity of the aqueous mix increases rapidly, but during this period the mix has little rigidity and can be stirred, poured, cast or otherwise worked to give a desired shape of the first product. The onset of the second setting stage is indicated by gelling of the mix at which point the material has sufficient rigidity to prevent further working. During the course of the second stage the material develops greater mechanical strength. The end of the second stage may be arbitrarily defined as the time at which the cement has sufficient rigidity appropriate to a particular use. The two periods of setting are known as the working time, $t_w$, and the setting time $t_s$. It has been found that the setting characteristics are determined by the particular glass composition employed to effect cross-linking of the poly-carboxylic acid material and that furthermore, the period between gelling and setting of the material in general corresponds to the period within which gelling occurs.

In many applications it is necessary to provide a cement having a relatively long period before gelling occurs so that ample time is provided for making the material. However, in providing a long working time, the period between gelling and setting is correspondingly extended and in many circumstances is excessive.

THE OBJECT OF THE INVENTION

The object of the invention is to minimize or overcome these disadvantages.

SUMMARY OF THE INVENTION

According to one aspect of the invention there is provided a glass composition adapted to provide cross-linking of a poly-carboxylic acid material when mixed with the material and contacted with water, said glass containing at least one divalent or polyvalent metal ion capable of cross-linking said acid material, and in which said glass includes or is associated with phosphorus pentoxide or a phosphate as herein defined, said phosphorus pentoxide or phosphate inhibiting the initial stages of setting of the acid material.

According to another aspect of the invention there is provided a dry pack mix for providing a water setting cement composition, including a polycarboxylic acid material, a glass containing at least one divalent or polyvalent metal capable, when in aqueous solution, of cross-linking the acid material, and phosphorus pentoxide or a phosphate as herein defined included in or associated with said glass said phosphorus pentoxide or phosphate inhibiting the initial stages of setting of the acid material.

According to a further aspect of the invention there is provided a method of controlling the setting characteristics of a polycarboxylic acid cement mixture, the cross-linking agent comprising or being provided by a glass composition containing at least one divalent or polyvalent metal ion, the method including incorporating in said mixture a proportion of a phosphate material sufficient to delay the initial stages of setting of the acid material.

DETAILED DESCRIPTION OF THE PREFERRED EMBODIMENTS

As well as improving the setting characteristics of cement employing at present in use, the phosphate treatment process also permits the use of glasses which, e.g. because of their high solubility, were previously considered unsuitable for use in such cements. Thus, for example, the process permits the use of glasses with a relatively low opacity to x-rays and which are therefore particularly advantageous in the preparation of splint bandages.

The final properties of such glass set cements are affected by the homogeneity of the wet mixture prior to setting. In order to permit thorough mixing of the glass and the polycarboxylic acid, typically polyacrylic acid, it is necessary that the working time is of sufficient length dependent on the method of mixing or working and on the particular application to which the cement is to be put. By extending the working time of such cement mixtures the phosphate treatment described herein greatly increases the range of usable glass compositions.

The term 'phosphate' as used herein is understood to include not only orthophosphate, but also metaphosphate, pyrophosphate and polyphosphate.

To ensure uniform and reproducible setting of a cement composition it is preferred to incorporate the phosphate material in the glass itself. Typically the glass may be of zinc oxide/boric oxide/alumina.

The phosphating technique however is not of course limited to such glasses and may be employed e.g. with fluoroalumino silicate glasses, or glasses incorporating calcium oxide, magnesium oxide, zirconium oxide, titanium oxide or mixtures thereof. The phosphate, or phosphorus pentoxide may be deposited on the surface of the glass, or a solid phosphate or a phosphate solution may be added to the cement/glass mix immediately prior to setting.

One method of incorporating a phosphate in the glass material is to surface coat the glass with phosphorus pentoxide by a vapour phase process. The crushed glass is placed in a furnace and is exposed to phosphorus pentoxide vapour carried in a stream of oxygen at a temperature between 300° and 370° C. This provides a relatively low solubility borophosphate surface coating on the glass particles thus lowering the solubility of the glass during the early stages of the setting reaction. This extends the working time $t_w$ without significantly affecting the setting time $t_s$. It has been found that the larger sieve fractions treated in this way provide the desired effect on the setting process. However, the glass particle size should not be less than 5 microns since such small particle sizes do not allow penetration of the phosphorus pentoxide vapour below the surface layer of the powder. The solubility effect appears to be superimposed on the effect of phosphate on the reaction.

An alternative method of incorporating a phosphate in the material is the addition of an ammonium phosphate, typically ammonium dihydrogen phosphate, to the glass. This may be achieved in one of two methods.

In the first method ammonium dihydrogen phosphate powder is mixed with the powdered glass and sufficient water is added to the dry mix to form a paste. The paste is thoroughly stirred to provide an homogeneous mixture and the water is subsequently removed by drying in an oven at a temperature not exceeding 500° C. and the resultant cake is lightly ground to powder. Typically between 1 and 10 weight % ammonium dihydrogen phosphate is added to the glass by this method. It has been found that the temperature at which drying is carried out has only a secondary effect on the setting characteristics of a cement incorporating the glass.

The second method of ammonium phosphate addition is aqueous solution coating of the glass. In this method a dilute aqueous solute of an ammonium phosphate is added to a dry glass/polycarboxylic acid mixture. Typically, 2 ml of a 0.05 to 0.25 Molar solution of an ammonium phosphate is added to 4 g of a suitable mix of glass and PAA.

In both these techniques, i.e. slurry coating and solution coating, the excess water may be removed in a number of ways. Advantageously the material is spray dried. Alternative methods include freeze drying and fluidised bed drying. Where oven drying is employed it is preferred to bake the treated glass at 300° C. as this provides optimum setting characteristics of the subsequent cement mix.

In a further application a solid phosphate, or an aqueous solution thereof, may be added to a glass/polycarboxylic acid mix immediately prior to setting. Alternatively a dry mix of an untreated glass and a polycarboxylic acid may be prepared and then treated with a dilute phosphate solution which also provides other necessary water to initiate the setting reaction. In a further embodiment an aqueous solution of phosphoric acid may be employed in place of a phosphate.

The phosphate treatment process described herein may be used to prepare cement for various purposes. For example the process may be used in the preparation of x-ray transparent or opaque orthopaedic cements, dental cements, x-ray opaque screen incorporating a lead glass, bone replacement cements and structural cements. The treatment is applicable to all glass compositions which can be employed to cross-link such cements. Thus, it is applicable not only to water soluble or partially coated soluble glasses, but also to insoluble glasses of the ion leachable type. It should also be understood that the phosphate treated glasses may be employed both with powdered, i.e. solid, polycarboxylic acids and aqueous solutions thereof.

The following Examples illustrate the invention.

EXAMPLE I

A glass was prepared having the composition
Zinc oxide: 48.6 mole%
Boric oxide: 48.2 mole%
Alumina: 3.2 mole%

Samples of the powdered glass were wet mixed with ammonium dihydrogen phosphate powder followed by oven drying at 300° C. The ammonium phosphate was added to the glass to give 1%, 2%, 3%, 4% and 10% ammonium dihydrogen phosphate by weight. The working and setting time of polyacrylic acid cement using the glass were measured and are summerised in the following table. The weight ratio of glass to cement was 3:1. The mix was divided into 4 g samples to each of which 2 ms liquid were added.

TABLE I

| Ammonium Phosphate % | Working Time secs. | Setting time mins. |
|---|---|---|
| 0 | 10 | 11 |
| 1 | 20 | 9 |
| 2 | 90 | 10 |
| 3 | 190 | 10 |
| 4 | 210 | 11 |
| 10 | 270 | 13 |

This demonstrates that the addition of a phosphate to the reaction mix considerably extends the working time without substantially affecting the setting time.

EXAMPLE II

Samples of the untreated glass composition of Example I were dry mixed with powdered polyacrylic acid in the weight ratio of 3:1. Water was added to 4 g portion of the mix followed by measured quantities of molar ammonium dihydrogen phosphate solution at room temperature. The working and setting times of the samples were measured and are summerised in the following table.

TABLE 2

| Solution added - ml | Working time secs. | Setting time mins. |
|---|---|---|
| 0 | 10 | 9.5 |
| 0.1 | 20 | 9.5 |
| 0.2 | 30 | 10.5 |
| 0.3 | 100 | 10.75 |
| 0.4 | 150 | 12.0 |
| 0.5 | 390 | 16.0 |

This Example again demonstrates the effect of phosphate addition on the working time of cement mixes. The setting time although slightly increased is still conveniently short for most applications.

EXAMPLE III

This Example demonstrates the effect of various alkaline metal salts on the setting characteristics of the cement compositions. The glass composition of Example I and II was employed.

The glass was dry mixed with powdered polyacrylic acid and the mix was divided into 4 g lots. 2 mls of a 0.25 M solution of various salts were added to the samples, the results being summarized below.

TABLE 3

| Salt | Working Time | Setting Time mins. |
|---|---|---|
| None | 10 seconds | 9.5 |
| $NH_4H_2PO_4$ | 6.5 min | 16.0 |
| $(NH_4)_2HPO_4$ | 3.5 min | 12.0 |
| $(NH_4)_3PO_4$ | 2.0 min | 9.5 |
| $NH_4NO_3$ | 10 seconds | 6.0 |
| $NH_4CL$ | 10 seconds | 4.5 |
| $NaH_2PO_4$ | 6.0 min | 16.5 |
| $NaNO_3$ | 10 seconds | 4.5 |

This Example demonstrates that materials other than phosphate have very little effect on the setting rate of the cement composition.

In a further embodiment a phosphate may be added to the constituent of the glass prior to fusion to form the glass.

In one embodiment of the invention a dry pack mix of a polycarboxylic acid and a switchable glass treated or untreated with a phosphate material may be provided. When required for use water or an aqueous solution of a phosphate respectively are added to the mix to form the cement.

The term glass as employed herein is understood to include not only true glass systems but also partially and completely devitrified or phase separated glass.

We claim:

1. A method of controlling the setting characteristics of an aqueous polycarboxylic acid cement mixture, the cross-linking agent comprising or being provided by a crushed glass composition selected from the group consisting of zinc oxide/boric oxide/alumina and fluoroaluminoborosilicate, the method including incorporating in said mixture a phosphate material by treating the surface of said crushed glass with sufficient phosphorus pentoxide in vapor phase or coating the surface of said crushed glass with sufficient alkaline metal phosphate salt selected from the group consisting of orthophosphate, metaphosphate, pyrophosphate and polyphosphate so as to extend the working time without substantially extending the setting time of the acid material.

2. A method as claimed in claim 1 wherein said glass incorporates as a glass modifying oxide calcium oxide, magnesium oxide, zirconium oxide, titanium oxide or mixtures thereof.

3. A method as claimed in claim 2 wherein the oxide is titanium oxide.

4. A method as claimed in any one of claims 1, 2 or 3, in which said glass is treated by being exposed to phosphorus pentoxide in vapor phase.

5. A method as claimed in any one of claims 1, 2 or 3, in which said glass is coated with a phosphate salt from an aqueous solution.

6. A method as claimed in claim 5, in which said phosphate is an ammonium phosphate.

7. A method as claimed in any one of claims 1, 2 or 3, in which said glass is coated with a solid phosphate salt from a liquid slurry.

* * * * *